US00RE35070E

United States Patent [19]

Fitzmorris

[11] E Patent Number: Re. 35,070

[45] Reissued Date of Patent: Oct. 24, 1995

[54] ROOT CANAL FILLING DEVICE INCLUDING RELEASABLY REUSABLE INSERTER TOOL

[75] Inventor: Bernard A. Fitzmorris, Washington, D.C.

[73] Assignee: John T. McSpadden, Chattanooga, Tenn.

[21] Appl. No.: 126,798

[22] Filed: Sep. 24, 1993

Related U.S. Patent Documents

Reissue of:

[64] Patent No.: 5,051,093
Issued: Sep. 24, 1991
Appl. No.: 361,438
Filed: Jun. 5, 1989

[51] Int. Cl.[6] ..... A61C 5/02

[52] U.S. Cl. ..... 433/224

[58] Field of Search ..... 433/81, 102, 224

[56] References Cited

U.S. PATENT DOCUMENTS

| | | | |
|---|---|---|---|
| 674,419 | 5/1901 | Kinsman | 433/224 |
| 1,463,963 | 8/1923 | Miller | 433/224 |
| 1,469,992 | 10/1923 | Card | 433/81 |
| 3,318,000 | 5/1967 | Paris | 433/224 |
| 3,813,779 | 6/1974 | Tosti | 433/224 |
| 4,480,996 | 11/1984 | Crovatto | 433/81 |
| 4,746,292 | 5/1988 | Johnson | 433/224 |
| 4,758,156 | 7/1988 | Johnson | 433/81 |
| 4,882,407 | 11/1989 | Riazi | 526/340.2 |
| 4,894,011 | 1/1990 | Johnson | 433/81 |
| 4,931,096 | 6/1990 | Fujisawa et al. | 106/35 |
| 5,083,923 | 1/1992 | McSpadden | 433/224 |
| 5,165,893 | 11/1992 | Thompson | 433/224 |

OTHER PUBLICATIONS

Thermafil, "The Perfect Apical Seal", (1 page brochure).
Thermafil, "Commonly Asked Questions about Thermafil", (1 pg. brochure).
Thermafil, "Directions for Use of Thermafil", (1 page brochure).

*Primary Examiner*—Cary E. O'Connor
*Attorney, Agent, or Firm*—Luedeka, Neely & Graham

[57] ABSTRACT

A root canal filler assembly including a single use obturator and a multiple use elongate inserter tool is disclosed. The oburator includes a metallic core and a plasticizable coating, preferably formed of gutta percha. One end of the metallic core extends beyond the plasticizable coating to support a connector assembly. The multiple use inserter tool is removably connectable to the oburator to insert, remove, adjust, and reposition the obturator in a root canal. The inserter tool includes at one end a connector assembly which engages the obturator and at the other end a handle to facilitate manipulation of the assembly by the dentist. The elongate inserter tool may be reused as required, both to remove or reposition a previously inserted obturator and to insert additional obturators in other root canals.

A method of filling and sealing a root canal employing the disclosed root canal filler assembly is also provided.

44 Claims, 3 Drawing Sheets

ROOT CANAL FILLING DEVICE INCLUDING RELEASABLY REUSABLE INSERTER TOOL

Matter enclosed in heavy brackets [ ] appears in the original patent but forms no part of this reissue specification; matter printed in italics indicates the additions made by reissue.

TECHNICAL FIELD

The present invention relates generally to devices and methods for treating root canals. More particularly, the present invention relates to a two part root canal treatment device including a single use portion for filling the apical end of a root canal and a multiple use portion of which temporarily engages the single use portion to insert it into the root canal and is then removed.

BACKGROUND OF THE INVENTION

A tooth is a calcified structure that includes a crown portion connected to one or more relatively long root portions which extend through the gum and into the jawbone. The roots of a tooth usually curve slightly as they extend away from the tooth crown to culminate in a relatively thin apex. Each tooth root includes a root canal with rough-surfaced inner walls. In a healthy tooth, the pulp chamber and root canal are filled with pulp, which includes the tooth blood supply and nerve. Dental problems which involve the tooth roots, particularly the root canals, are quite common.

When a tooth becomes diseased or damaged as a result of infection, abscess formation, periodontal disease; trauma to the tooth or a deep cavity, removal of the tooth's pulp may be the only way to save the tooth. The damaged or diseased pulp, which contains the nerves and blood supply for the tooth, can cause additional damage or infect surrounding tissues unless the tooth is treated to remove the affected pulp. Treatment of the tooth involves making an opening in the the crown of the tooth to allow access to the pulp in the tooth pulp chamber and root. The pulp is removed, and the canal and pulp chamber cleaned thoroughly and medicated, if required, to prevent further infection. Once all infection is gone, the root canal and pulp chamber are filled and sealed, and the crown of the tooth is restored. The extent of the crown restoration necessary may vary from a simple "filing" if the tooth is structurally sound to a full crown replacement supported by one or more posts placed in the root canal.

The root canal treatment preferred by endodontists involves filling the root canal and pulp chamber with an inert biocompatible material to prevent further complications. Unless the pulp is removed and the root canal refilled with a biocompatible, inert material, the damaged pulp could serve as a medium for bacteria or act as a "foreign body," and the root could become further inflamed or infected. It is especially important to insure that the root apex is sealed and filled properly to prevent the intrusion of fluids from the tissue surrounding the root into the canal, or to prevent the extrusion of filler material into this tissue.

When problems with the tooth root and the root canal arise, there may be damage to the crown of the tooth as well. Crown damage could also occur during drilling of the tooth to treat the root canal if the structural integrity of the tooth has been affected by the disease, trauma or infection that originally caused the root canal problem. To restore the crown may require the placement of one or more posts within the tooth that extend into the root canal, to anchor a crown or other restorative work. Such posts are used not only to assist in the total restoration and rehabilitation of the tooth. but are sometimes placed in the root canal as an additional tooth support, even when crown restoration is not required. Posts that are located in the root canal are typically cemented in place after the pulp is removed before the root canal is filled. Consequently, their removal can be difficult.

In some cases, additional treatment or restorative work must be performed on the tooth some time after the root canal has been filled and sealed. This may require the removal of the root canal filling to allow the necessary treatment or restoration of the tooth. Until now, root canal fillings could only be removed with considerable manipulation of the root canal and tooth. These procedures and the use of potentially toxic substances, such as chloroform, increase the attendant risk of damage to surrounding tissues resulting from available root canal treatments.

Various and diverse devices and methods have been used to fill and repair root canals. Filler points or cones made from gutta percha or silver, posts screwed into the jawbone, and obturators, such as those marketed under the name THERMAFIL by Tulsa Dental Products, have been used to fill the apical portion of the root canal. Pastes and injectable gutta percha have been used both in conjunction with the above devices and separately to fill root canals. However, all of these devices and methods have inherent disadvantages. are biocompatible, pure gutta percha points are overly flexible and lack rigidity, which causes them to bind in the root canal during insertion. Consequently, a gutta percha point often cannot be inserted as far into the root canal as it should go. In addition, it is possible to insert such a point farther into the root canal than is desirable. If this occurs, a pure gutta percha point is extremely difficult to retrieve and remove. Other available pliable biocompatible materials, such as injectable gutta percha and pastes, are difficult to control at the root apex and may be forced through the root apex. In addition, the injectable pastes sometimes tend to resorb.

Kinsman U.S. Pat. No. 674,419 and Miller U.S. Pat. No. 1,463,963 are representative of early solutions to the problem of filling a root canal. These patents disclose the use of gutta percha points having metallic cores for this purpose. Although these fillers have more rigidity and may be somewhat easier to control than pure gutta percha points, the metallic core points described in these patents are difficult to retrieve if pushed too far into the root canal. If the canal requires retreatment at a later date, moreover, this type of gutta percha metal point is very difficult to remove.

Some rigid metallic fillers, for example silver points, tend to corrode over time, as they are not highly biocompatible with root canal environment. These elongated point devices, moreover, are not flexible and cannot adequately conform to the curvature of the tooth root canal to fill and seal the canal effectively. Also, it may be difficult to place a post in the same canal with a silver point or cone. If the pulp is replaced with a silver point which extends substantially the entire length of the canal, the incisal or occlusal end of the point must be removed to accommodate a post. Removal is usually accomplished by drilling. However, not only is it difficult to drill through the silver, but such drilling vibrates the silver point so that damage to the apical seal is extremely likely. Consequently. It is necessary to notch the silver point prior to insertion in the canal so that the top of the point may be broken off with dental pliers rather than drilled. Finally, the retrieval and removal of these points for subsequent treatment of the tooth is not easily accomplished.

One recently proposed root canal filler device is a one piece endodontic obturator which includes a calibrated stainless steel carrier shaped like a standard endodontic file and coated on one end with alpha gutta percha. This carrier is provided in a range of different sizes corresponding to standard endodontic file sizes. A handle on one end of the carrier assists the dentist in the insertion of this obturator into the root canal. An endodontic file must first be inserted in the root canal to obtain the approximate distance the obturator must be inserted into the root canal. Once this distance is determined. A rubber stop on the carrier is positioned at the calibration on the carrier corresponding to this distance. The gutta percha portion of the obturator is then heated until it begins to expand and becomes plasticized, and the obturator is inserted into the root canal to the level indicated by the rubber stop. The stainless steel carrier provided with this device is significantly longer than required to fill the root canal. Consequently, the excess carrier shaft must be cut off and removed. This is done with a fissure but in a high speed hand piece while the shaft is in the root canal. The excess shaft, handle and stop are then removed to allow vertical condensation of the gutta percha.

While the aforementioned endodontic obturator represents an improvement over previously available root canal filler devices, it still suffers from some significant disadvantages. Because the gutta percha tip is heated prior to insertion into the root canal. it is possible to push the end of the stainless steel carrier shaft through the warmed gutta percha during insertion so that exposed metal rather than plastic gutta percha contacts the root apex. If too much force is exerted during insertion. not only could the metal be exposed, but the metal shaft could actually penetrate the root canal apex. In neither instance would an effective apical root canal seal be formed Severing the carrier shaft to the proper length with a fissure bur in a high speed hand piece after the obturator has been inserted into the root canal subjects the obturator to undesirable high speed vibrations that could vibrate the device loose and also traumatize the tooth. Cutting this carrier shaft inside the mouth is also more difficult for the dentist. In addition, this prior art endodontic obturator requires special treatment so that the root canal can accommodate both the obturator and a post, if one is required for restorative work. The stainless steel carrier shaft must be properly notched somewhat below the level of he rubber stop and handle prior to insertion and the shah broken off after insertion. Too large a notch will weaken the shaft so that it could break during insertion. while too small a notch may prevent breakage of the shaft at the proper time.

Moreover, the removal of this obturator from the root canal can only be accomplished with difficulty. If the obturator is notched and separated well down into the root canal, its removal is virtually impossible. The handle portion of the obturator is permanently removed when the carrier shaft is severed, and, therefore, cannot be reconnected to the shaft. As a result, removal of the obturator requires the application of heat or solvents to the gutta percha and instruments to the carrier shaft to extract them from the root canal. Consequently, subsequent treatment a tool canal into which such an obturator for has been inserted can be performed only after a series of steps potentially traumatizing to the root canal, tooth and surrounding tissue.

Finally, if the aforementioned obturator is inadvertently thrust past the apical foramen, it is almost impossible to pull the metal core back into the root canal without leaving the already plasticized gutta percha behind.

Another prior art root canal filler is described in Tosti U.S. Pat. No. 3,813,779 discloses a threaded post which is screwed through the tooth and into the jawbone to fill the root canal and anchor the tooth. Apart from the likelihood of unnecessary trauma to the tooth and severe complication should the procedure not be properly performed, this device is not likely to provide an effective root canal seal.

The prior art devices for filling root canals, therefore. suffer from numerous drawbacks. Often, these devices are too flexible so that positioning and repositioning them is difficult. More rigid devices are unable to adequately fill and seal the apical region of the root canal as they can not conform to the curvature of the tooth root. Many of the devices are inserted, positioned, or customized within the root canals in ways that unduly traumatize the tooth, gums, jawbone, and surrounding mouth areas. Moreover, if these devices are improperly manipulated, further trauma and complications could result. Available tools used to insert available root canal filler pins or points are not easy to use. None of the known devices and tools for filling root canals, moreover, is easy to use, permits the filler to be first attached and subsequently reattached to an inserter tool for adjustment or removal of the filler, or employs a reusable inserter.

Thus, the prior art fails to provide a root canal filler device including a single use substantially flexible filling cone or obturator that conforms to both the relatively long length and the curvature of a tooth root canal to effectively seal and fill the root canal and that can be adjusted to the proper length after radiographic confirmation of placement within the root canal, wherein the obturator is removably reattachable to a multiple use inserter tool whereby the obturator is inserted into a root canal so thai after the inserter tool has been separated from the obturator, the inserter can be easily reattached to the obturator to reposition or remove it, as required. There is a need, therefore, for such a two part root canal filler device including a single use obturator for effectively filling and sealing the root canal and a multiple use insertion tool for inserting and removing the obturator as required for the treatment and ongoing management of root canal problems.

SUMMARY OF THE INVENTION

It is an object of the present invention, therefore, to provide a two part root canal filler device that includes a single use filler portion removably reattachable to a multiple use inserter portion which facilitates both the initial filling and sealing of a root canal and the ongoing management of root canal treatment.

It is another object of the present invention to provide a root canal filling device that includes a filler portion that can be cut to the specific length required to fill and seal the root canal at a location outside the mouth.

It is another object of the present invention to provide a root canal filling device that includes a filler portion that will effectively seal the root canal without corroding or irritating the surrounding tissue.

It is another object of the present invention to provide a two part root canal filling device that includes an single use filler portion including a relatively flexible coating formed of a pliable biocompatible material which substantially conforms to the shape of the root canal when inserted therein and a relatively rigid core formed of a biocompatible metal which is releasably engaged by a multiple use inserter tool which guides the filler portion to its proper position in the root canal.

It is another object of the present invention to provide a root canal filling device that includes a single use, elongate, cone shaped filler portion that produces a consistent, effective apical seal, allows for easy placement and adjustment during obturation of the root canal, and is easily retrieved if the root canal requires retreating.

It is another object of the present invention to provide a root canal filling device which both effectively seals and fills a root canal and accommodates a dental post in the canal.

It is a further object of the present invention to provide a method of filling a root canal wherein a single use root canal filler formed of a biocompatible flexible coating and a biocompatible rigid core is inserted into the canal of a tooth root by a temporarily attached multiple use inserter tool to seal and fill the root canal along a desired distance from the apex, and the inserter tool is easily and nontraumatically removed from the canal.

It is yet a further object of the present invention to provide a method of filling a root canal wherein the canal is quickly and effectively sealed and filled to the proper level in a manner which minimizes trauma to the tooth and mouth tissues.

It is a still further object of the present invention to provide a treatment method for tooth root canals whereby a single root canal can be effectively filled and sealed during a first treatment and the filler easily removed and the canal retreated during one or more subsequent treatments.

The aforesaid objects are achieved by providing a two part root canal filler assembly that includes a single use obturator which is sufficiently flexible and plastic to be inserted into the root canal to conform to the shape of the canal so that it seals the apex and fills the canal to a predetermined distance from the apex. A multiple use inserter tool which temporarily and removably engages the obturator is provided to assist the endodontist in inserting one or more such obturators into the root canal and positioning the obturator or obturators properly within the canal to fill the canal as required. The inserter tool is then easily disengaged from the obturator and removed from the root canal with substantially no trauma to the canal or surrounding structures. The obturator includes an elongated metal core which is coated with a flexible plasticizable material along its apical end. A portion of the core extends beyond the coating to form an uncoated obturator shaft, which includes a connector assembly and terminates in a point at its insertion end. The inserter tool is an elongated rod, one end of which is a connector end with a connector assembly which engages the corresponding connector assembly on the insertion end of the obturator shaft. The opposite end of the inserter tool includes a handle having substantially the same configuration as a conventional root canal file and a measuring means for ascertaining the distance the inserter tool has been inserted into the canal.

The present invention additionally provides a method for filling and sealing a tooth root canal using the above-described assembly, wherein the obturator threaded shaft is screwed into the threaded recess in the inserter tool to temporarily connect it to the inserter tool, and this assembly is inserted into the canal of the root of a tooth so that the coated apical end of the obturator seals and fills the apex of the root canal to the required distance. Heat is applied to the plasticizable coating to cause it to become plastic and conform to the irregular surfaces of the root canal, thus insuring that the canal is completely filled and sealed. The inserter tool is then disconnected from the obturator threaded shaft and removed from the canal. If removal of the obturator is subsequently required, the inserter tool is simply reinserted into the canal and reconnected to the obturator so that the connector assemblies are teengaged. Because repeated removal of the obturator can be accomplished readily and easily, any cutting required to shorten the obturator can be done outside the dental patient's mouth.

Various additional advantages and Features of novelty which characterize the invention are further pointed out in the claims that Follow. However, for a better understanding of the invention and it advantages, reference should be made to the accompanying drawings and descriptive matter which illustrate and describe preferred embodiments of the invention.

DETAILED DESCRIPTION OF PREFERRED EMBODIMENTS

The root canal filler assembly of the present invention provides the endodontic specialist with a treatment device and method for easily and effectively performing the initial treatment and managing the ongoing care of problems associated with the roots of the teeth. In the past, the treatment and care of these problems has been neither easy nor always as effective as could be desired. Until the present invention, once a root canal filler was inserted into the canal it could be retrieved only with difficulty, which usually resulted in some degree of trauma to the tooth and surrounding structures in the dental patient's mouth. The present invention offers an alternative to previously available root canal devices and filling procedures that is not only nontraumatic and, therefore, more easily tolerated by the dental patient, but is also extremely effective and reliable in filling and sealing the root canal.

Figure 1:
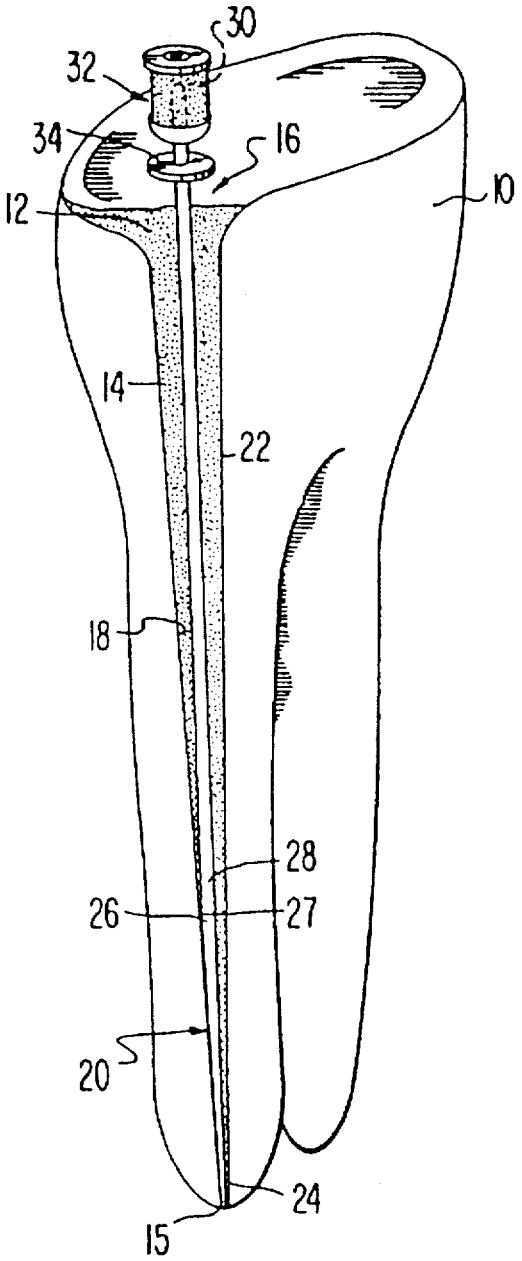
FIG. 1 is a cut away side perspective view of the root canal filler assembly of the present invention inserted in the root canal of a tooth, wherein the assembly components are temporarily connected.
Figure 2:
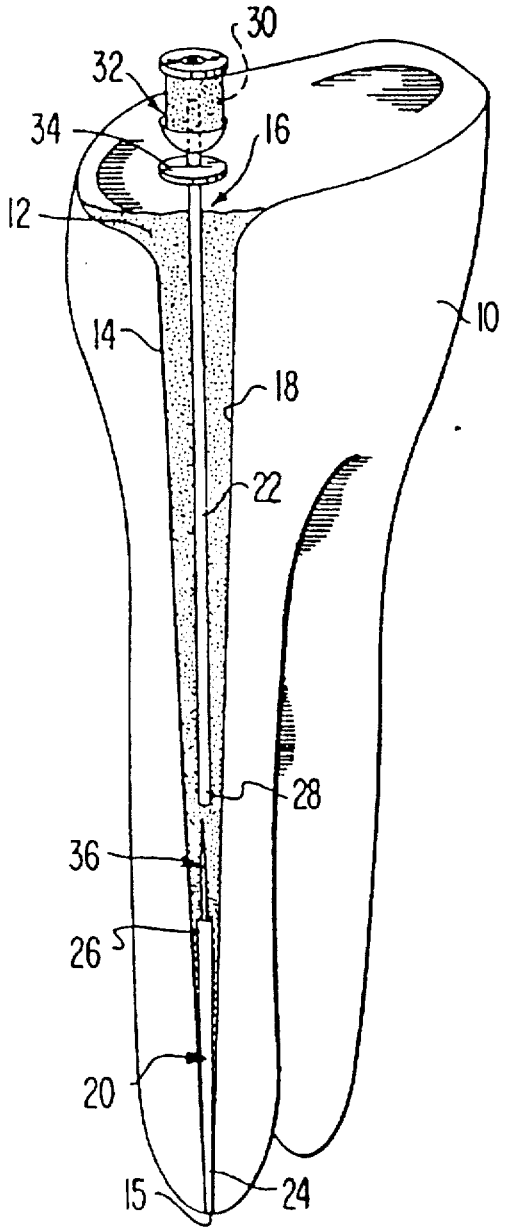
FIG. 2 is a cut away side perspective view of the root canal assembly of the present invention wherein the assembly components have been disconnected.

Referring to the drawings, the root canal filler assembly of the present invention is shown n in FIGS. 1 and 2 inserted in the root canal of tooth 10. Although the tooth shown is a lower tooth, the assembly is equally effective in filling the roots of upper teeth. The tooth shown in FIGS. 1 and 2 has had much of the crown removed to provide access to the pulp chamber 12 and root canal 14. The pulp, including the blood supply and tooth nerve has already been removed from the root canal as part of the treatment of the tooth shown in FIGS. 1 and 2, so that the canal is substantially cleared of this tissue. FIGS. 1 and 2 show a perspective side view of the tooth 10 with a portion of the tooth removed to illustrate clearly the placement of the present root canal filler assembly 16 in the canal 14.

Although the walls 18 of root canal 14 are shown as being relatively straight and smooth, in actuality the canal may curve somewhat, and the walls have a rough irregular surface. These features have presented obstacles to the proper filling and sealing of root canals which the present invention has overcome.

The root canal filler assembly 16 is illustrated in FIG. 1 as it would appear following the initial insertion of obturator 20, the filler portion of the assembly, into the apex 15 of the root canal 14. The obturator 20 is shown temporarily connected to the inserter portion, inserter tool 22. The obturator 20 has an apical end 24, which contacts the apex 15 of the root canal, and an inserter end 26, which will be described in more detail below in connection with FIG. 3. The inserter tool has a connector end which engages the insertion end 26 of the obturator 20 at joint 27 within the root canal. The opposite end 30 of the inserter tool 22 extends beyond the pulp chamber 12 to support a handle 32.

Although other handle configurations could be employed, the three part substantially cylindrical arrangement shown in FIGS. 1 and 2 is preferred. This configuration is substantially identical to that of a conventional root canal file and, as a result, provides the dentist with a familiar structure. The tactile familiarity provided by this particular handle further enhances the efficiency with which the assembly can be used to fill and otherwise treat root canals, which must, of necessity, be performed in very limited space. The handle may be formed of metal, rubber, or a plastic, such as polyvinyl chloride (PVC). However, a metal handle would only be selected if the root canal filler device was intended to be used with a heat applicator.

The root canal filler assembly also preferably includes a stop 34 slidably mounted on the inserter tool 22 to move axially along the inserter between the handle 32 and the top of the pulp chamber 12. Stop 34, which is preferably formed of rubber or a similar flexible, substantially inert material, is employed as a measuring gauge to facilitate the assessment of the correct placement of the obturator 20 at the root canal apex 15. The manner in which stop 34 performs this function will be explained herein below.

Figure 3:
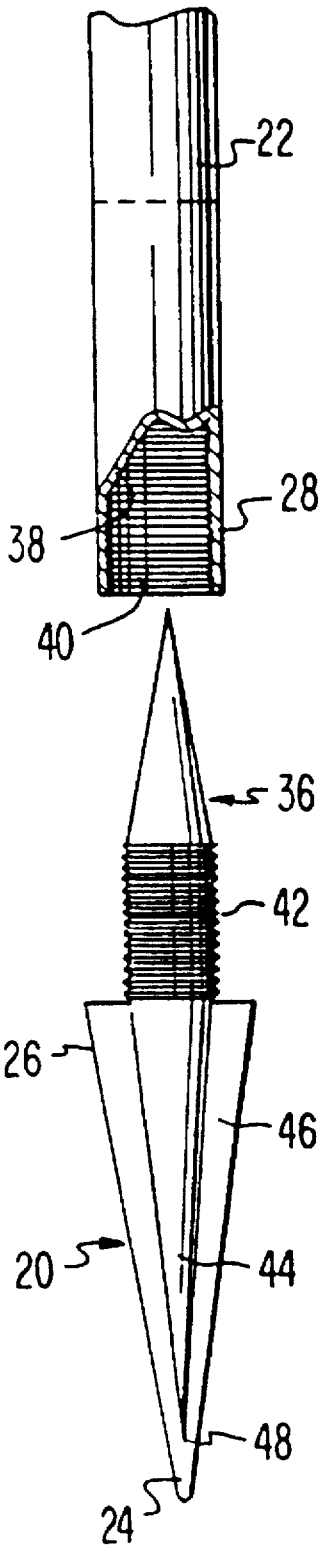
FIG. 3 is a partially cut away side view of the connector structures of the two part root canal filler assembly of the present invention.

Unlike the prior art, the present root canal filler assembly includes two major components which are temporarily connected prior to their insertion into the root canal and are then disconnected within the root canal once obturator 20 has been placed in an optimum sealing position. FIG. 2 illustrates the components of the root canal filler assembly 16 after they have been disconnected, but before the inserter Tool 22 has been removed from the root canal. Connector end 28 of inserter tool 22 has been removed from its connection with inserter end 26 of the obturator 20 and is shown spaced beyond the terminus 36 of obturalor 20. Terminus 36, which will be discussed in detail in connection with FIG. 3, is telescopingly received inside the inserter tool 22 when the obturator 20 is connected to the inserter tool and, thus, is not visible when these components are connected as shown in FIG. 1. Once the inserter tool 22 is separated from the obturator 20 as shown in FIG. 2. the obturator is generally intended to remain permanently in place in the root canal 14. However, achieving the proper position of the obturator in the canal may at times be difficult due, for example, to the curvature of the tooth root or the angle of access to the root canal. Removal of the obturator from the root canal and its reinsertion into the root canal are greatly simplified by the present invention. The inserter tool 22 is simply reconnected to the obturator 20 to form the unitary structure of FIG. 1, and the handle 32 can be employed to easily extract the assembly from the canal. Reinsertion into the canal is likewise readily accomplished. This arrangement is especially well suited to root canals that previously were extremely difficult to fill and seal in a manner which achieved an optimum apical seal.

In addition, the temporary easy disconnect-reconnect feature of the present root canal filler assembly 16 eliminates the traumatic separation which accompanies the unitary permanently connected prior art filler devices.

Filler 3 illustrates in detail the temporary connect-disconnect feature of the present root canal filler assembly which renders the inserter tool 22 capable of repeated use. As noted above, the assembly 16 includes two parts: a multiple use inserter tool 22 and a single use obturator 20. The inserter tool is designed to be reused a number of times to insert a member of obturators into one or more tooth root canals during a single treatment session. The filling of teeth with multiple root canals may require the insertion of more than one obturator like obturator 20. In this case, a single inserter tool 22 can be connected to each obturator in turn to position it in the root canal and then disconnected and removed from the canal. The inserter tool 22 can also be cleaned and sterilized for reuse at a later time.

The inserter tool 22 is an elongated shaft and, as discussed in connection with FIGS. 1 and 2, includes a handle receiving end 30 and a connector end 28. The inserter tool shaft may be formed of metal, plastic or any similar sterilizable material having sufficient rigidity to provide a positive connection with obturator 20 and to insert the obturator into the apex 15 of root canal 14. An inserter tool having a shaft that is approximately 12 to 15 mm in length has been found to function most effectively.

The connector end 28 of inserter tool is formed with a recess 38 which is shown partially cut away in FIG. 3. Recess 38 includes one part of a connector assembly 40 which temporarily, but securely, engages a corresponding connector assembly 42 on the obturator 20. Although the preferred type of connector assembly is formed from a the mating threaded connector assemblies 40 and 42 shown in FIG. 3, other types of connectors that provide the secure temporary connection, disconnection and reconnection required by the present invention could also be employed. The longitudinal extent of recess 38 should be sufficient to accommodate the entire terminus 36 of obturator 20, including the connector assembly 42.

The obturator 20 has a configuration which generally resembles that of a conventional hand held root canal file. This allows obturator 20 to be held securely by hand without resort to the cotton pliers customarily required for the insertion of root canal filler structures while it is connected to inserter tool 22 prior to insertion in the mouth. Obturator 20 preferably has a generally cone-shaped configuration to conform substantially to the size and shape of the endodontic files common employed to file root canals. The obturator 20 includes a rigid core 44 which is coated with a flexible plasticizable coating 46, which is preferably a high melting (beta) gutta percha. This flexible plasticizable coating extends a substantial distance along the core 44 from an apex 24 to terminate just short of the connector assembly 42. The core extends beyond coating 46 to support connector assembly 42 and terminates in terminus 36, which preferably has the inverted cone shape shown in FIG. 3. This shape has been found particular effective in guiding and engaging the obturator connector assembly 42 into engagement with inserter tool 22 during reconnection of the assembly within the root canal. The obturator rigid core 44, therefore, is covered with the plasticizable coating 46 from its apical end 48 to the connector assembly 42.

It is preferred to form the rigid core 44 from a biocompatible, inert material having sufficient rigidity to allow easy insertion of the obturator into even a very curved root canal. Preferred materials include metals such as titanium and stainless steel. Fluting the exterior of the rigid core material can facilitate condensation of the plasticizable coating as will be discussed below.

The apical end 48 of core 44 is located close enough to obturator coating apex 24 to provide sufficient rigidity to insert obturator 20 into the root canal all the way to root canal apex 15 without obturator apex 24 binding or bending back on itself. The core apical end 48 does not extend all the ay to the obturator coating apex and, therefore, is not likely to be pushed through the coating during insertion of the obturator into the root canal.

Since tooth root canals are not uniform in size, but vary, obturator 20 is preferably provided in a range of sizes which approximate the sizes of conventional root canal files. Additionally, the configuration of the obturator 20 can be custom sized to fit a root canal by adding different thicknesses of coating or gutta percha to the rigid core 44. The width and degree of taper of the obturator can be made to correspond to the width and degree of taper of the last endodontic file used to file the root canal.

The condensation techniques with which the root canal filler assembly 16 will be used will determine whether additional gutta percha or like plasticizable material will be required to completely fill the root canal. If regular lateral condensation techniques are employed, accessory gutta percha cones will be required. However, if heat is applied to the obturator through the handle by a heat applicator, additional gutta percha would not be required. Instead, the heated obturator could be spun clockwise to condense the warmed gutta percha apically and laterally. For this to be successful, however, the rigid core 44 must be properly fluted. Alternatively, a lubricated hollow condenser could be employed after removal of the handle.

Once a specific size obturator is selected, it is connected to the inserter tool 22 by inserting the terminus 36 into recess 38 until the corresponding connectors on the obturator and inserter tool are engaged. If connector assemblies 40 and 42 are mating threads as shown in FIG. 3, once the threads of recess 38 contact the threads of obturator core 44, these structures can simply be screwed together.

After the obturator 28 is optimally positioned within the root canal, it is disconnected from inserter tool 22 by unscrewing the inserter tool to disengage the threads of recess 38 from the exterior threads of the obturator 20. If obturator 20 subsequently must be repositioned or removed, it can be easily reconnected to inserter tool 22 by repeating this process.

The obturator 20, which is substantially cone-shaped to conform to the shape of the root canal, may also be referred to as a filler cone. The rigid core 44 is formed of metal, preferably titanium. Implant grade titanium is used for metallic core 44 because of its very high biocompatibility and its resistance to corrosion. The use of such material prevents complications arising from the inadvertent placement of obturator 20 too far into the root canal or from the inadvertent exposure of the metal within the root canal. The plasticizable coating 46 is preferably formed of gutta percha because it is malleable and can be easily plasticized and expands to conform to the various nooks, crannies, and irregularities in the root canal surface. However, any suitable thermoplastic material which is biocompatible and has the physical properties required to provide an effective root canal seal and filler could also be employed.

Disk-shaped stop 34 (FIGS. 1 and 2), as described above, is used as a measuring device to provide an approximate measurement of the length of the approximately 18 mm in length. Thus, stop 34 is positioned on inserter tool 22 approximately 18 mm from the end of filler assembly 16 as measured from the apex 24 of obturator 20. When stop 34 approaches the crown of the tooth during insertion of the assembly, the dentist knows that the apical environment of the root canal has been reached by the obturator apex 24. This reduces the incidence of long or short placement of obturator 20 within the root canal. Alternatively, inserter tool 22 may be provided with integral numbered or colorcoded markings extending axially from handle 32 to estimate the length of a root canal.

Although obturator 20 is selected to be as close in size to the diameter of the root canal as possible, it will never fit exactly. Moreover, since the root canal walls are not perfectly smooth, steps must be taken to insure that the plasticizable coating 46 will completely fill the canal. Lateral condensation techniques can be used to fill all of the irregularities in a root canal. According to this method, an obturator 20 is inserted into a root canal. After it is properly placed within the root canal, a conventional spreader tool (not shown) is inserted into the root canal and is forced between the wall and the obturator to put lateral pressure on the plasticizable coating 46 to contort and mold it into the irregularities of the root canal surface. After the spreader tool is removed, if the root canal is not filled, a conventional accessory gulta percha cone may be inserted into the root canal and the process repeated until the root canal is completely filled. A conventional plugger tool (not shown) may also be used vertically to compress excess plasticizable coating 46, thereby further insuring complete sealing of the root canal and the root apex.

The present root canal filler assembly is vastly superior to prior art devices. The obturator 20 is strong enough to be placed in a root canal without bending back on itself or binding on the walls of the canal. The removable, reusable inserter tool 22 permits easy adjustment and correction of the ebturator placement if it is placed too far or not far enough into the root canal. Additionally, the obturator 20 can be placed m the canal and subsequently removed using inserter tool 22 to provide space for a post, if one is necessary to restore the endodontically treated teeth. Removal and repositioning of the obturator 20 are simplified by the provision of the corresponding connector assemblies 40 and 42 on of the obturator 20 and the inserter tool 22. This arrangement allows the obturator and inserter tool to be easily connected, separated, and reconnected as required. The obturator can also be retrieved relatively easily for subsequent retreatment of the root canal.

The present root canal filler assembly is easily adapted to accommodate dental posts, if they are required to support crown restoration following filling and sealing of the root canal. To accomplish this, the obturator may be made in two specific lengths, one for use in a root canal without a dental post and one for use with a dental post. When a root canal is to be filled without a post, obturator 20 is provided with a plasticizable gutta percha coating 46 approximately 10 mm in length as measured from obturator apex 24. Approximately ½ mm of gutta percha protrudes pat the apex 48 of the rigid titanium obturator core 44, and the remaining 9½ mm of gutta percha extend along titanium core 44 to the connector assembly 42. The distance between the end of coating 46 and terminus 36 of the obturator core is about 17 mm. Preferably, substantially the entire 17 mm of the titanium obturator core is provided with threads or another connector structure.

When the root canal is to have a post inserted after it is filled, obturator 20 preferably is provided with about 5 mm of plasticizable coating 46, approximately ⅓ mm of this protrudes past the core apex 4–8, and the remaining 4⅔ mm covers the rigid core 44. In this instance, preferably approximately 1–3 mm of rigid (titanium) core 44 extends beyond the coating 4–6. Most of this length will preferably support the connector assembly 41 and will terminate in pointed terminus 36. This particular obturator is specifically sized so that it does not require cutting after insertion into the root canal to accommodate a post. This eliminates completely the traumatic notching and twisting of the obturator to shorten it after it has been inserted into the root canal required by prior art root canal filling devices.

Obturator 20 is preferably inserted into root canal 14 unheated and then may be laterally condensed without heating to spread the gutta percha so that it fills the canal. Alternatively, optimal filling of the canal may be achieved by using a heating device attached to inserter tool 22 by a clip or the like to conduct a standard, controlled amount of heat from the inserter tool through the obturator along the metal core 44 to soften the gutta percha coating 46 before condensing the gutta percha with a spreader or plugger lubricated with alcohol. Heating the gutta percha outer coating 46 after obturator 20 is inserted into the root canal eliminates the possibility that the titanium core will be pushed out of the gutta percha coating or that the gutta percha will separate from the titanium during insertion of the filler assembly into the root canal as is likely with prior art devices.

Figure 4:
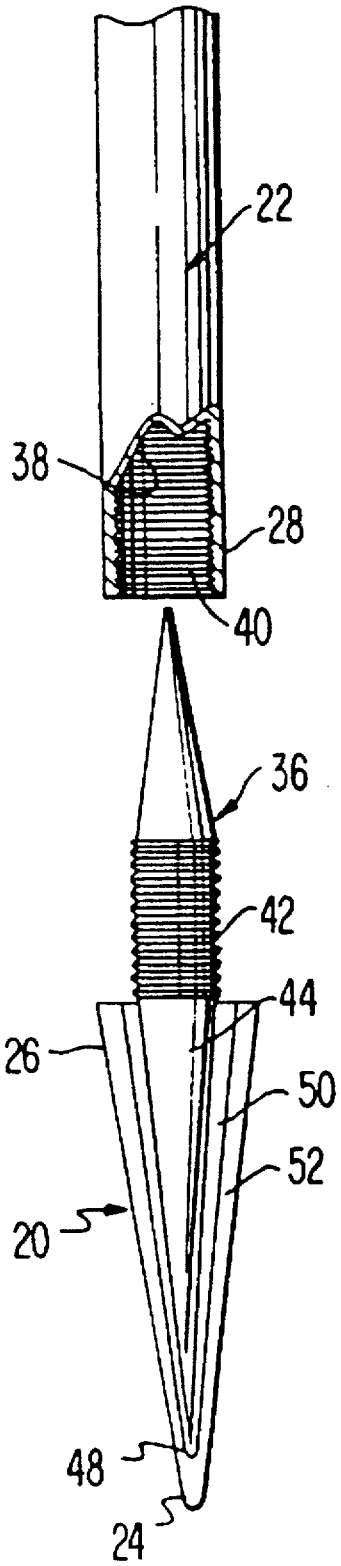
FIG. 4 is a partially cut away side view of another embodiment of the two part root canal filler assembly of the present invention.

In one alternative embodiment shown in FIG. 4, plasticizable coating 46, includes two layers of plasticizable material, one of which has a higher melting point than the other. It is preferred to form the inner layer 50 of high melting gutta percha and the outer layer 52 of low melting gutta percha. Ibis facilitates the use of heating devices instead of or in addition to lateral condensation techniques to spread the gutta percha to seal and fill the canal effectively. A heating device, similar to those made by Hygienic Corporation, can be employed to heat the filler assembly 16. The low melting gutta percha outer layer 52 will become plastic and flow to fill all of the root canal wall surface irregularities. P The high melting gutta percha inner layer will not become plastic at the same temperature and, therefore, will continue to provide some rigidity to the apex 24 and to provide a protective layer around the apical tip 48 of the titanium metal core. Forming the coating 46 of two layers allows the heating of the coating to a well controlled predetermined temperature which is sufficiently high to plasticize outer layer 52 without plasticizing inner layer 52. This arrangement also permits the heating of the filler assembly prior to insertion in a root canal without the risk of exposing the metal core which is inherent in prior art filler devices. The rigid metal core 44 will be protected by the layer 50 of high melting gutta percha and will not be easily pushed through the high melting gutta percha coating layer 50 to leave an unsealed exposed section of titanium. The use of differentially melting outer layer 52 and inner layer 50 permits even an uncontrolled heat source, such as a Bunsen burner or an alcohol torch to be used to heat the gutta percha coating. Even such an uncontrolled heat source is unlikely to plasticize inner layer 50. Heating may also be combined with lateral condensation techniques to plasticize the two layer gutta percha coating and assist its condensation so that the root canal is completely filled and sealed.

In another form of the present invention, a coating of metal plasma may be sprayed on the metal core 44, thereby roughening and increasing the core surface area to provide a better retentive surface for the gutta percha or other plasticizable coating. Alternatively, the metal may simply be sandblasted to create the necessary retentire surface roughness.

Figure 5A:
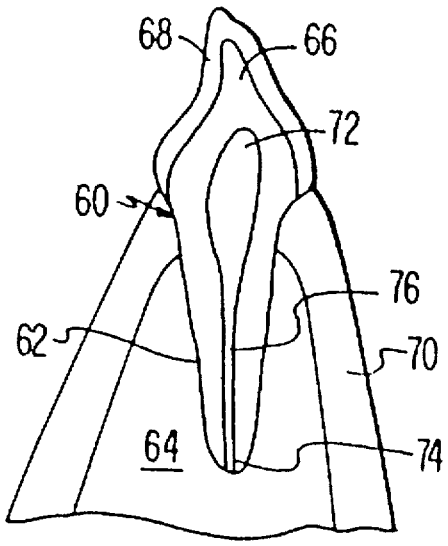
FIGS. 5a–5d illustrate the root canal filling method of the present invention.

A root canal can be filled with the assembly of the present invention using a series of simple steps which are illustrated in FIGS. 5a–5d. FIG. 5a shows a crossectional side view of a tooth 60 in place in the mouth. The tooth root 62 extends well into the jaw bone 64. The opposite end of the tooth terminates in a crown 66 covered with a layer of enamel 68. Gum tissue 70 covers the jaw bone 64 and helps to hold the tooth securely in place. A pulp chamber 72 is located in the center of the tooth and extends longitudinally to the root apex 74 to form a root canal 76. If the pulp becomes damaged as a result of infection, trauma, disease or the like, it must be removed to prevent further damage to the tooth and surrounding tissues.

Figure 5B:
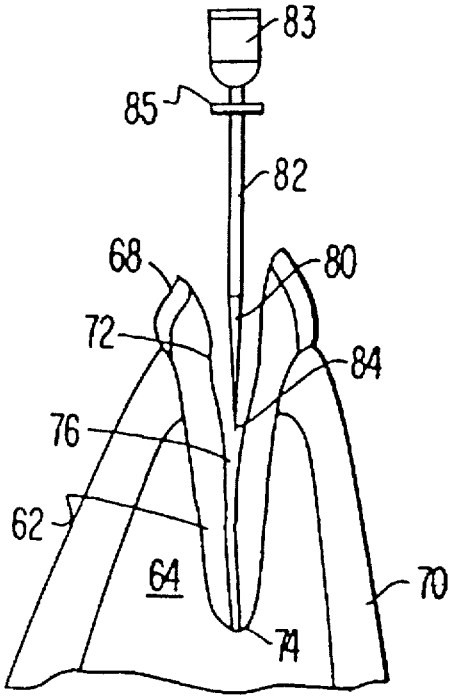

Removal of the pulp is accomplished by drilling through the tooth crown 66 to reach the pulp chamber 72. The opening formed must be large enough to provide adequate access to the pulp chamber to allow complete removal of the damaged or diseased pulp and cleaning of the pulp chamber and root canal. FIG. 5b illustrates a tooth which has been drilled to remove a portion of the crown 66 and expose the pulp chamber 72. The amount of tooth crown removed can range from a relatively small section to the entire crown, depending upon the integrity of the tooth. The extent to which the crown must be removed will determine whether one or more dental posts will be required to support crown restoration performed subsequent to the root canal treatment. As discussed above, the requirement for a post will affect the length filling cone or obturator selected to fill the canal.

A filler cone or obturator 80 of the appropriate length is selected and connected to an inserter tool 82 by inserting pointed terminus of the obturator into the recess in the inserter tool as discussed above in connection with FIGS. 1 to 3. The obturator 80 is secured to inserter tool 82. The handle 83 of the inserter tool is then used to guide the obturator into root canal 76, as shown in FIG. 5b, by first inserting the obturator apex 84 into the canal. As indicated above, because of the stiffness of the apex 84, it will not bind or bend back on itself during insertion. As long as obturator 80 remains connected to inserter tool 82 the obturator can be positioned, repositioned, adjusted, or removed from root canal 76 as necessary merely by manipulating the inserter tool.

Figure 5C:
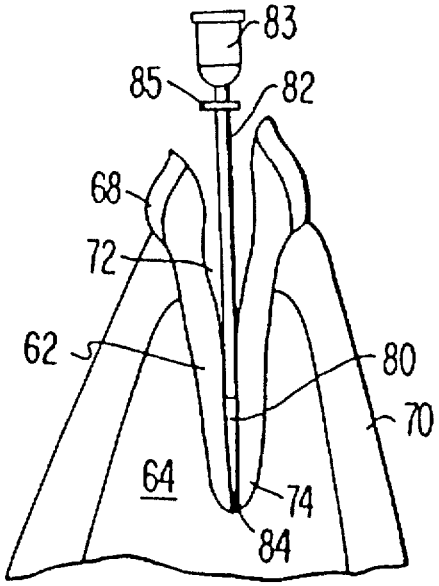

The assembly is inserted into the root canal so that the desired length of obturator 80 can be determined, either by positioning a slidable stop 85 or using calibrations on the inserter tool 82 as described in connection with FIG. 1. The assembly is then removed from the dental patients's mouth, and the excess length of obturator titanium core (not shown) is cut off, preferably using a Joe Dondy disc or similar tool. Ideally, after cutting, the obturator core extends approximately 2 to 3 mm above the gutta percha coating into the tooth pulp chamber when the apex 84 of the obturator 80 is properly placed in the root canal apex 74, as shown in FIG. 5c. This eliminates the possibility of vibrating and shaking loose the obturator as may occur if a bur is used to cut the obturator after placement in the root canal. Additionally, it is much easier to cut the obturator outside the mouth rather than after the obturator is inserted into the pulp chamber of the root canal where the cutting can become very messy.

Once the obturator 80 is properly positioned in the root canal as shown in FIG. 5c. the obturator plasticizable coating may be heated to a predetermined temperature to plasticize it so that it expands to fill and seal the root canal. Heating may be accomplished using any of various heating devices adapted to heat the coating in the root canal. Lateral or vertical condensation techniques may also be used, either in addition to or instead of heating. These techniques involve inserting a spreader or plugger into the root canal to force the gutta percha or other plasticizable coating into all of the surface areas of the root canal.

After obturator 80 is properly positioned in root canal 76, as shown in FIG. 5c, inserter tool 82 is separated from the obturator by disconnecting the respective connector assemblies on the inserter tool and the obturator. If a single obturator 80 is inserted and condensed and does not fill the root canal to the desired extent, additional obturators may be connected to the inserter tool and then inserted and condensed as necessary until the root canal is filled.

Once the root canal is filled to the necessary level, the inserter tool 82 can be removed simply by disconnecting it from the obturator and pulling it out of the root canal. If it is necessary to reposition obturator 80 after inserter tool 82 has been removed, the inserter tool 82 12 is easily reinserted into the root canal to engage obturator 80. The preferred obturator and inserter tool configuration shown in FIG. 3 facilitates the engagement of these components. The two components are then reconnected, and the appropriate adjustment performed.

Figure 5D:
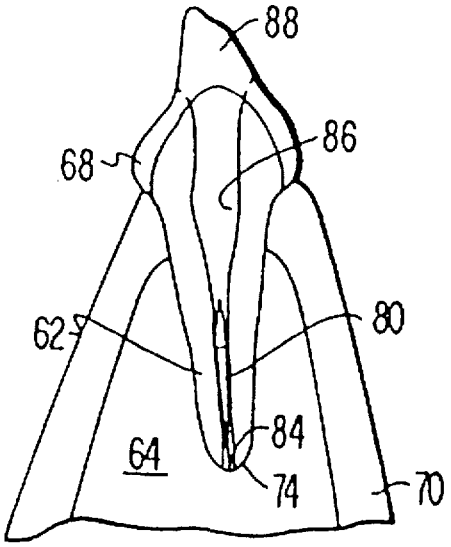

After obturator 80 is located in its final, desired position, the root canal 76 must be sealed and the tooth crown restored with a restoration 88 as shown in FIG. 5d. A small removable brightly colored "cap" of plastic or gutta percha can be made to place over and cover the threads of the connector assembly 42 placement of the obturator to prevent cement or other restoration materials from blocking access to the threads if it became necessary to re-attach the inserter tool at some future time.

Restoration of the crown will, of course, depend on the extent to which the crown was removed lo provide access to the root canal.

If a post is required to support crown restoration, the post can be inserted after one or more obturators have been placed as required to fill the apical portion of root canal. If a post is to be inserted into the root canal at a later time, the gutta percha sealant 86 can be seared off down to the level of the obturator 80.

Numerous characteristics, advantages, and embodiments of the invention have been described in detail in the foregoing description with reference to the accompanying drawings. However, the disclosure is illustrative only and the invention is not limited to the precise illustrated embodiments. Various changes and modifications may be effected therein by one skilled in the art without departing from the scope or spirit of the invention.

INDUSTRIAL APPLICABILITY

The root canal filler assembly of the present invention is a substantial improvement over known root canal filling devices. The filler assembly of the present intention will find its primary application and use in the field of endodontics where it may be effectively employed in initially treating and in managing the ongoing treatment of root canals.

I claim:

1. A root canal filter assembly for inserting a biocompatible filler material into the canal of the root of a tooth to fill and seal the canal following removal of the tooth pulp and treatment of the canal, said filler assembly comprising:

(a) single use filler means conforming substantially to the configuration of the root canal to fill and seal the root canal from the apex of the root to a desired distance away from the apex, said single use filler means having an apical end, and an insertion end, wherein said insertion end includes a threaded filler connector assembly, and (b) multiple use inserter means for inserting said filler means into the root canal and properly positioning said filler means in the root canal, said multiple use inserter means having a connector end and a handle end wherein said connector end includes a threaded inserter connector assembly configured to threadedly and removably engage the threaded filler connector assembly of said filler means.

2. The root canal filler assembly of claim 1, wherein said filler means includes a relatively rigid longitudinal core portion and a relatively flexible plasticizable coating portion extending axially along said core portion from said apical end to terminate short of said insertion end to leave said core portion exposed al the insertion end of said filler means.

3. The root canal filler assembly of claim 2, wherein said filler connector assembly is positioned on said exposed core portion.

4. The root canal filler assembly of claim 3, wherein said inserter connector assembly is positioned interiorly of the connector end of said insertion means.

5. The root canal filler assembly of claim 4, wherein said inserter connector assembly and said filler connector assembly comprise correspondingly threaded sections of said inserter means and said filler means is threadedly engaged by said inserter means.

6. The root canal filler assembly of claim 5, wherein said filler means core portion is formed of metal.

7. The root canal filler assembly of claim 6, wherein said filler means coating portion is formed of gutta percha.

8. The root canal filler assembly of claim 5, wherein said filler means coating portion comprises two layers of differentially melting plasticizable material, said innermost layer having a higher melting point than said outermost layer.

9. The root canal filler assembly of claim 8, wherein the innermost of said two layers comprises high melting gutta percha and the outmost of said two layers comprises low melting gutta percha.

10. The root canal filler assembly of claim 1, wherein said inserter means further includes handle means located at the handle end thereof to facilitate the insertion and manipulation of said inserter means in a root canal.

11. The root canal filler assembly of claim 10, wherein said inserter means further includes measuring means for measuring the distance said filler assembly has been inserted into said root canal and assessing proper placement of the filler assembly in the root canal.

12. The root canal filler assembly of claim 11, wherein said measuring means comprises a stop axially slidable along said inserter means.

13. A filling device for refilling a tooth root canal with a canal filling during treatment of the tooth to permit the canal filling to be easily inserted, positioned, and removed, said filling device comprising:

an elongate filler cone having first and second ends and comprising a relatively narrow tip portion formed at said first end, said elongate filler cone being insertable and adjustable within and removable from the tooth root canal;

removable elongate insertion means for inserting, adjusting, repositioning, and removing said elongate filler cone in the root canal, said removable elongate insertion means comprising first and second ends and a handle portion formed at said first end, and said removable elongate insertion means being reusable: and connection means disposed at said second end of said removable elongate insertion means for releasably connecting said removable elongate insertion means to said second end of said elongate filler cone such that said elongate filler cone can be connected to, removed from, and reconnected said removable elongate insertion means as required.

14. A root canal filling device according to claim 13 wherein said elongate filler cone is formed with external threads on said second end and wherein said connection means comprises a hollows internally threaded portion formed at said second end of said removable elongate insertion means, said elongate filler cone and said removable elongate insertion means being releasably, threadably connectable and reconnectable together.

15. A root canal filling device according to claim 14 wherein said second end of said elongate filler cone comprises a relatively narrow tip portion receivable in said hollow internally threaded portion to facilitate connecting said elongate filler cone to said removable elongate insertion means.

16. A root canal filling device according to claim 13 wherein said relatively narrow tip portion formed at said first end of said elongate filler cone is sufficiently rigid to resist binding or bending back when said elongate filler cone is inserted into a root canal.

17. A root canal filling device according to claim 13 wherein said removable elongate insertion means comprises a rigid inserter shaft.

18. A root canal filling device according to claim 17 wherein said inserter shaft is formed of metal.

19. A root canal filling device according to claim 17 wherein said inserter shaft is formed of plastic.

20. A root canal filling device according to claim 17 further comprising measuring means for indicating the approximate length of the root canal to thereby reduce the incidence of long or short placement of said elongate filler cone within the root canal.

21. A root canal filling device according to claim 20 wherein said measuring means comprise a rubber disk slidably mounted on said inserter shaft near said first end below said handle.

22. A root canal filling device according to claim 13 wherein said handle is shaped like a root canal file.

23. A root canal filling device according to claim 13 wherein said handle is formed of plastic.

24. A root canal filling device according to claim 13 wherein said handle is formed of rubber.

25. A root canal filling device according to claim 13 wherein said elongate filler cone comprises an inner core layer and an outer shell layer.

26. A root canal filling device according to claim 25 wherein said inner core layer is formed of metal.

27. A root canal filling device according to claim 26 wherein said inner core layer is formed of manlure.

28. A root canal filling device according to claim wherein said outer shell layer is formed of a thermoplastic material.

29. A root canal filling device according to claim 28 wherein said outer shell layer is formed of gutta percha.

30. A root canal filling device according to claim 25 wherein said elongate filler cone further includes a retentive surface formed on said inner core layer.

31. A method of filling the root canal of a tooth with a biocompatible filler after the tooth has been opened to expose the root canal and the canal has been cleared of diseased or damaged pulp comprising the steps of:

(a) selecting an appropriately sized obturator means including an elongated rigid core portion, a flexible plasticizable coating portion covering said core portion to extend from one end of said core portion axially along said core portion, and a threaded connector assembly at the other end of said core portion for filling and sealing the apical end of the root canal:

(b) temporarily connecting the threaded connector assembly of said obturator means to a correspondingly threaded connector assembly on the connector end of an inserter means for inserting said obturator means into the root canal by screwing said connector assemblies together to form a tool canal filler assembly: (c) inserting said root canal filler assembly into the cleared root canal so that the coating portion of the obturator means is positioned within the canal to fill and seal the apical end of the root canal:

(d) disconnecting the inserter means from the obturator means by unscrewing the inserter means threaded connector assembly from the obturator means threaded connector assembly; (e) removing said inserter means from the root canal to leave the obturator means in the root canal, thereby permitting said inserter means to be reused: and (f) sealing the portion of the root canal not filled by the obturator means and restoring the integrity of the tooth.

32. The method of filling a root canal described in claim 31, further including the steps of removing the seal formed in step (f), reinserting said inserter means into said root canal, screwing said threaded connector assembly of said obturator means into said threaded connector assembly of said inserter means, repositioning said obturator means, disconnecting said threaded connector assemblies, and removing said inserter means from said root canal.

33. The method of filling a root canal described in claim 31, further including the step of, after step (c) but before step (d), heating said obturator means to plasticize said plasticizable coating.

34. The method of filling a root canal described in claim 31, further including the step of, after step (e). inserting a support post into said root canal to extend from said obturator means to the tooth surface.

35. The method of filling a root canal described in claim 31, further including the step of, after step (c) but before step (d). using measuring means to measure the distance said assembly extends to said root canal.

*36. A biocompatible filler for insertion into the canal of the root of a tooth to fill and seal the canal following removal of tooth pulp and treatment of the canal, said filler comprising:*

*a relatively rigid longitudinal core; and*

*a relatively flexible plasticizable coating extending axially along at least a portion of said core, said plasticizable coating comprising an innermost layer and an outermost layer of differentially melting plasticizable material.*

*37. The filler of claim 36, wherein the innermost layer has a higher melting point than the outermost layer.*

*38. The filler of claim 36, wherein the innermost layer comprises high melting gutta perch and the outermost layer comprises low melting gutta percha.*

*39. The filler of claim 36, wherein the core is metal.*

*40. The filler of claim 39, further comprising a coating of metal plasma on the metal core underneath the innermost layer of gutta percha.*

*41. A relatively flexible, plasticizable biocompatible filler for insertion into the canal of a root of a tooth to fill and seal the canal following removal of tooth pulp and treatment of the canal, said filler comprising:*

*a first plasticizable material which is essentially solid at room temperature and which is spreadable in the canal under heat and/or mechanical action so as to flow therein;*

*a second plasticizable material which is essentially solid at room temperature and which is spreadable in the canal under heat and/or mechanical action so as to flow therein under substantially different conditions of heat and/or mechanical action as compared to said first plasticizable material, wherein said first and second plasticizable materials spread in the canal to fill the canal during a filling procedure, one spreading prior to the other.*

*42. The material of claim 41, wherein said first plasticizable material and said second plasticizable material have substantially different melting points.*

*43. The filler of claim 41, wherein said first plasticizable material comprises a relatively high melting point gutta percha and said second plasticizable material comprises a relatively low melting point gutta percha.*

*44. The filler of claim 41, wherein said first plasticizable material comprises an inner layer of relatively high melting point gutta percha and said second plasticizable material comprises an outer layer of relatively low melting point gutta percha surrounding the layer of relatively high melting point gutta percha.*

* * * * *

UNITED STATES PATENT AND TRADEMARK OFFICE

CERTIFICATE OF CORRECTION

PATENT NO. : Re. 35,070

DATED : Oct. 24, 1995

INVENTOR(S) : Bernard A. Fitzmorris

It is certified that error appears in the above-indentified patent and that said Letters Patent is hereby corrected as shown below:

Col. 3, line 11, after "determined" delete "." and insert --,--.

Col. 3, line 20, after "fissure" delete "but" and insert --bur--.

Col. 3, line 27, after "root canal" delete "." and insert --,--.

Col. 3, line 34, after "formed" delete "Severing" and insert --severing--.

Col. 3, line 45, after "insertion and the" delete "shah" and insert --shaft--.

Col. 3, line 43, "he" should read —the—.

Col. 3, line 47, after "insertion" delete "." and insert --,--.

Col. 3, line 58, after "treatment a" delete "tool" and insert --root--.

Col. 4, line 30, after "canal so" delete "thai" and insert --that--.

Col. 4, line 58, after "includes" delete "an" and insert --a--.

Col. 6, line 1, after "assemblies are" delete "teengaged" and insert --reengaged--.

Col. 6, line 7, after "claims that" delete "Follow" and insert --follow--.

UNITED STATES PATENT AND TRADEMARK OFFICE

CERTIFICATE OF CORRECTION

PATENT NO. : Re. 35,070

DATED : Oct. 24, 1995

INVENTOR(S) : Bernard A. Fitzmorris

It is certified that error appears in the above-indentified patent and that said Letters Patent is hereby corrected as shown below:

Col. 6, line 52, after "is shown" delete --n--.

Col. 7, line 45, "Tool" should be --tool".

Col. 7, line 48, after "36 of" delete "obturalor" and insert "obturator".

Col. 8, line 34, after "from" delete --a--.

Col. 8, line 51, after "files" delete "common" and insert --commonly--.

Col. 8, line 60, after "found" delete "particular" and insert --particularly--.

Col. 9, line 11, at the beginning of the line, delete "ay" and insert --way--.

Col. 10, line 28, after "accessory" delete "gulta" and insert --gutta--.

Col. 10, line 39, after "the" delete ebturator" and insert --obturator--.

Col. 10, line 41, after "placed" delete "m", and insert --in--.

Col 10, line 60, after "protrudes" delete "pat" and insert --past--.

UNITED STATES PATENT AND TRADEMARK OFFICE

CERTIFICATE OF CORRECTION

PATENT NO. : Re. 35,070

DATED : Oct. 24, 1995

INVENTOR(S) : Bernard A. Fitzmorris

It is certified that error appears in the above-indentified patent and that said Letters Patent is hereby corrected as shown below:

Col. 11, line 4, after "core apex" delete "4-8" and insert --48--.

Col. 11, line 7, after "coating" delete "4-6" and insert --46--.

Col. 11, line 8, after "assembly" delete "41" and insert --42--.

Col. 11, line 36, after "percha." delete "Ibis" and insert --This--.

Col. 11, line 43, after "irregularities." delete --P--.

Col. 12, line 4, after "necessary" delete "retentire" and insert --retentive--.

Col. 13, line 40, after "removed" delete "lo" and insert --to--.

Col. 13, line 61, after "present" delete "intention" and insert --invention--.

Col. 14, line 23, after "exposed" delete ""al" and insert --at--.

Col. 15, line 12, after "reconnected" insert --to--.

Col. 15, line 17, after "comprises a" delete "hollows" and insert --hollow--.

UNITED STATES PATENT AND TRADEMARK OFFICE

CERTIFICATE OF CORRECTION

PATENT NO. : Re. 35,070 Page 4 of 4

DATED : Oct. 24, 1995

INVENTOR(S) : Bernard A. Fitzmorris

It is certified that error appears in the above-indentified patent and that said Letters Patent is hereby corrected as shown below:

Col. 15, line 61, after "formed of" delete "manlure" and insert --titanium--.

Col 16, line 18, after "form a" delete "tool" and insert --root--.

Col. 16, line 51, after "(d)", delete --.--.

Col. 16, line 66, after "gutta" delete "perch" and insert --percha--.

Signed and Sealed this

Tenth Day of December, 1996

Bruce Lehman

*Attest:*

BRUCE LEHMAN

*Attesting Officer*

*Commissioner of Patents and Trademarks*